US009733189B2

(12) United States Patent
Maskrot et al.

(10) Patent No.: US 9,733,189 B2
(45) Date of Patent: Aug. 15, 2017

(54) SMOKE ANALYSIS CHARACTERIZATION CELL

(75) Inventors: Hicham Maskrot, Montlhery (FR); Jean-Baptiste Sirven, Paris (FR); Pascale Dewalle, Vernon (FR); Benoit Guizard, Creteil (FR)

(73) Assignee: COMMISSARIAT A L'ENERGIE ATOMIQUE ET AUX ENERGIES ALTERNATIVES (FR)

( * ) Notice: Subject to any disclaimer, the term of this patent is extended or adjusted under 35 U.S.C. 154(b) by 0 days.

(21) Appl. No.: 13/824,712

(22) PCT Filed: Oct. 27, 2011

(86) PCT No.: PCT/EP2011/068900
§ 371 (c)(1),
(2), (4) Date: Jun. 10, 2013

(87) PCT Pub. No.: WO2012/055978
PCT Pub. Date: May 3, 2012

(65) Prior Publication Data
US 2013/0280132 A1  Oct. 24, 2013

(30) Foreign Application Priority Data
Oct. 27, 2010  (FR) .................................. 10 58851

(51) Int. Cl.
*G01N 21/75* (2006.01)
*G01N 21/71* (2006.01)
(Continued)

(52) U.S. Cl.
CPC ............. *G01N 21/75* (2013.01); *G01N 21/05* (2013.01); *G01N 21/718* (2013.01);
(Continued)

(58) Field of Classification Search
CPC ............... B01J 2219/0875; G21K 1/00; G01N 21/3504; G01N 30/74; G01N 21/75
USPC .......................................................... 422/83
See application file for complete search history.

(56) References Cited

U.S. PATENT DOCUMENTS 3,985,505 A * 10/1976 Bredeweg .............. G01N 31/12
422/78
4,443,072 A    4/1984 Ballard
(Continued)

OTHER PUBLICATIONS

Amodeo T et al: "On-line determination of nanometric and sub-micrometric particle physicochemical characteristics using spectral imaging-aided Laser-Induced Breakdown Spectroscopy coupled with a Scanning Mobility Particle Sizer", vol. 64 No. 10, Oct. 1, 2009 pp. 1141-1152.

(Continued)

*Primary Examiner* — Dennis M White
*Assistant Examiner* — Bryan Kilpatrick
(74) *Attorney, Agent, or Firm* — Lerner, David, Littenberg, Krumholz & Mentlik, LLP

(57) ABSTRACT

The invention relates to a smoke analysis characterization cell employing optical spectroscopy, which comprises: a reaction chamber, an inlet orifice for injecting smoke into the reaction chamber; an outlet orifice for discharging the smoke from the reaction chamber; and an analysis window for the entry of a laser beam intended to form the plasma inside the reaction chamber, which cell is characterized in that the system further includes a blower for blowing an inert gas close to the analysis window; and a shielding gas injector for the shielded injection of the smoke into the reaction chamber, the shielding being provided by a jet of inert gas around the smoke.

18 Claims, 5 Drawing Sheets

(51) Int. Cl.
    *G01N 21/05*     (2006.01)
    *G01N 21/03*     (2006.01)
    *G01N 21/15*     (2006.01)
    G01N 21/3504    (2014.01)
    G01N 30/74      (2006.01)
    G21K 1/00       (2006.01)

(52) U.S. Cl.
    CPC ... *B01J 2219/0875* (2013.01); *G01N 21/0303* (2013.01); *G01N 21/3504* (2013.01); *G01N 30/74* (2013.01); *G01N 2021/151* (2013.01); *G21K 1/00* (2013.01)

(56) References Cited

U.S. PATENT DOCUMENTS 6,421,127 B1 *  7/2002  McAndrew et al. ......... 356/437
2005/0064600 A1 *  3/2005  Clark et al. .................... 436/106
2007/0075051 A1 *  4/2007  Morrisroe ................ H05H 1/30
                                                    219/121.52

OTHER PUBLICATIONS

Amodeo T et al: "On-line monitoring of composite nanoparticles synthesized in a pre-industrial laser pyrolysis reactor using Laser-Induced Breakdown Spectroscopy", vol. 63 No. 10, Oct. 1, 2008, pp. 1183-1190.

Dewalle P: "Caracterisation des aerosols emis par interaction laser-matiere dans le cadre d'experiences de decapage de peintures par laser", Apr. 10, 2009 pp. 1-49 (English translation of Abstract only).

French Search Report for Application No. FR 1058851 dated Mar. 11, 2011.

International Search Report for Application No. PCT/EP2011/068900 dated Nov. 28, 2011.

* cited by examiner

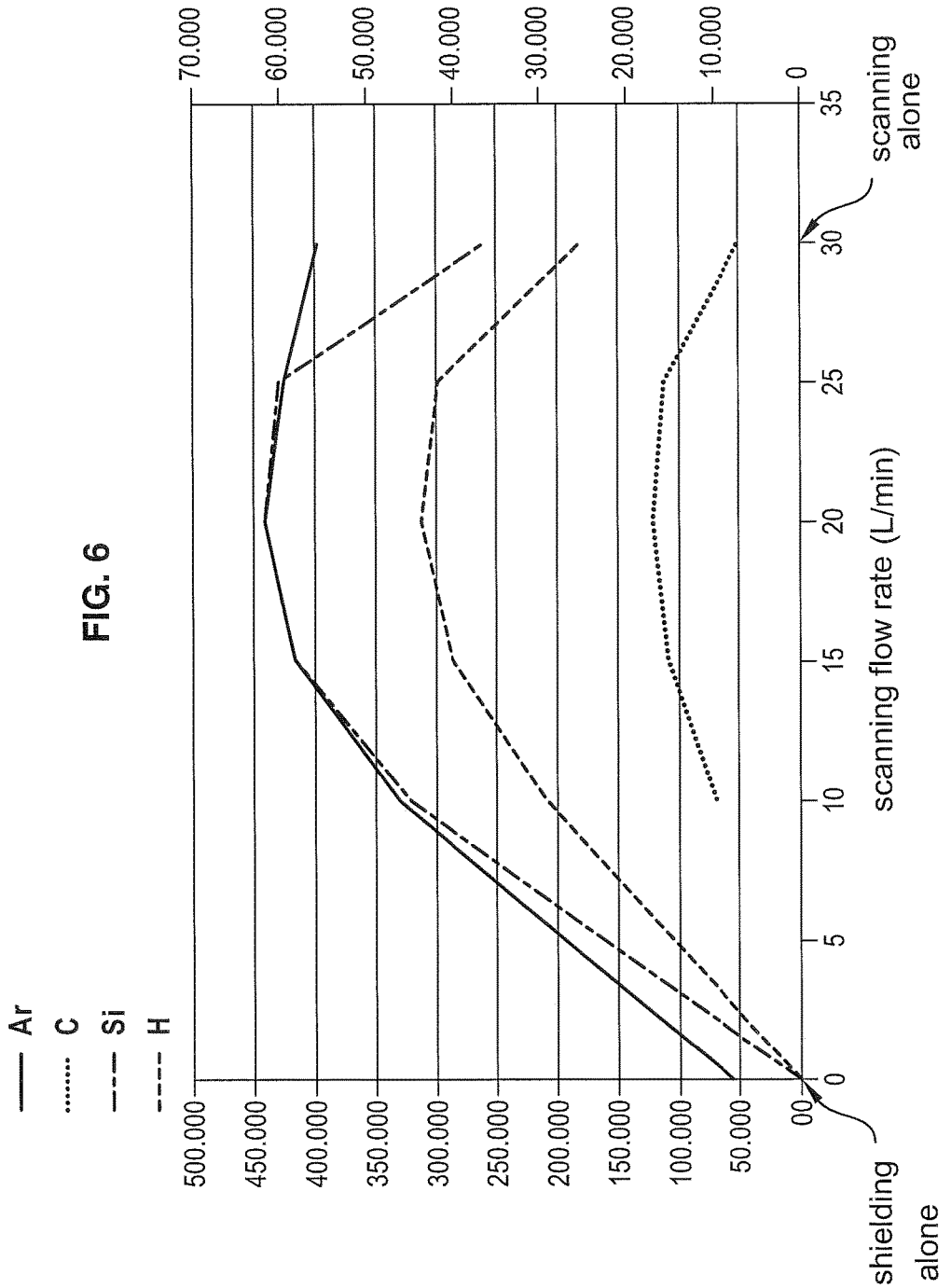

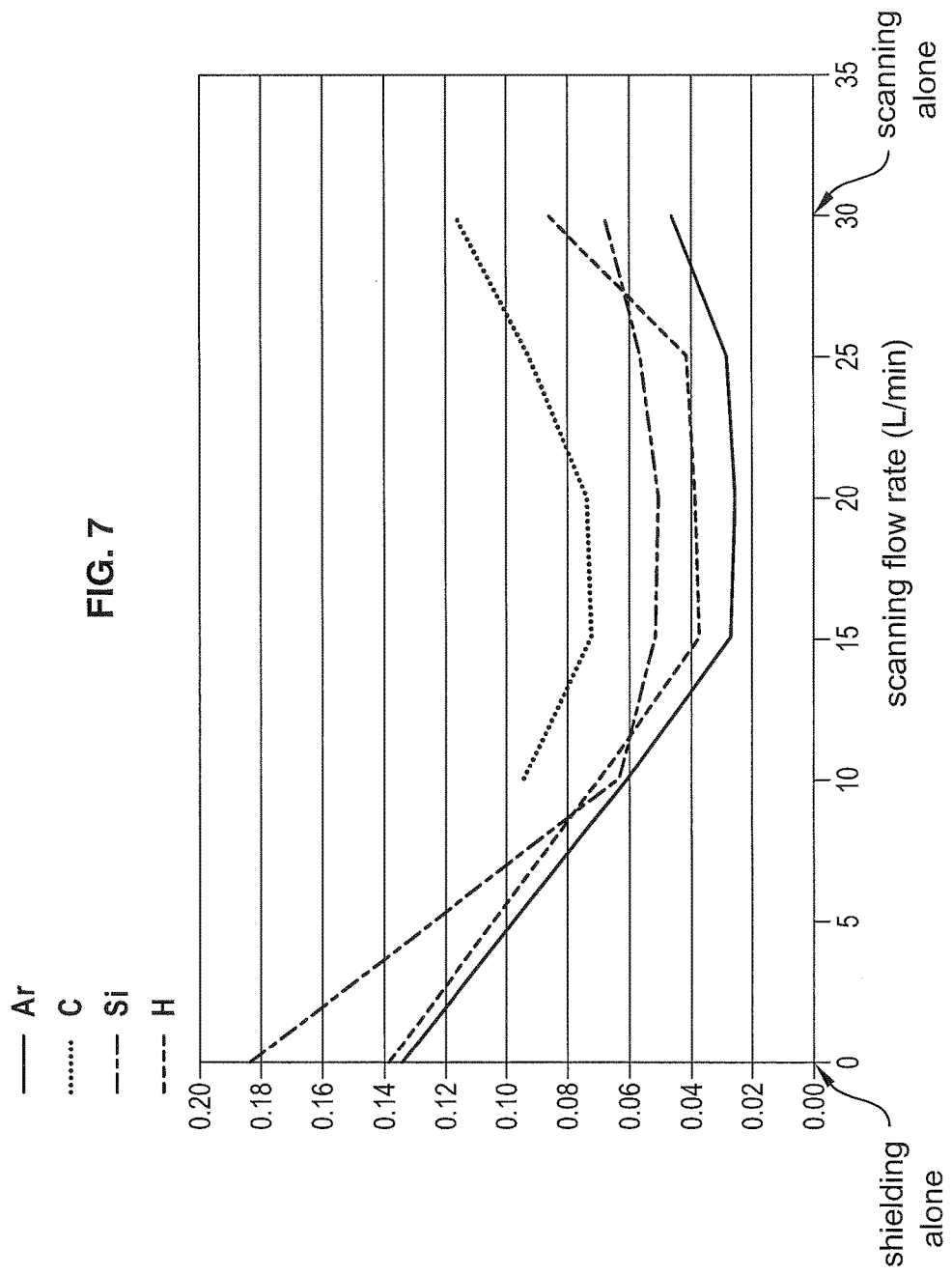

SMOKE ANALYSIS CHARACTERIZATION CELL

CROSS REFERENCE TO RELATED APPLICATIONS

The present application is a national phase entry under 35 U.S.C. §371 of International Application No. PCT/EP2011/068900, filed Oct. 27, 2011, published in French, which claims priority from French Patent Application No. 1058851, filed Oct. 27, 2010, the disclosures of which are incorporated by reference herein.

TECHNICAL FIELD

The invention relates to the field of online material analysis. The material analysed by these means can be in the form of an aerosol or gas charged with particles making up this material forming smoke.

More particularly, the invention relates to the field of optical analysis systems for the study of particles formed by pyrolysis inside a characterisation cell.

TECHNOLOGICAL BACKGROUND

The cell forming the subject matter of the invention can be associated with various known characterisation means such as:
- laser-induced fluorescence;
- fluorescence spectrometry;
- absorption spectrometry;
- Raman spectrometry;
- infrared spectrometry.

By way of non-limiting example, the following description is based on the use of laser-induced breakdown spectrometry, or LIBS analysis. This method consists in focussing a pulsed laser beam into a reactional mixture to be analysed and forming plasma which is analysed by emission spectrometry. This determines the composition of said reactional mixture. This technique is applied in the description hereinbelow to control of smoke coming from the production of nanometric particles by laser pyrolysis.

Figure 1:
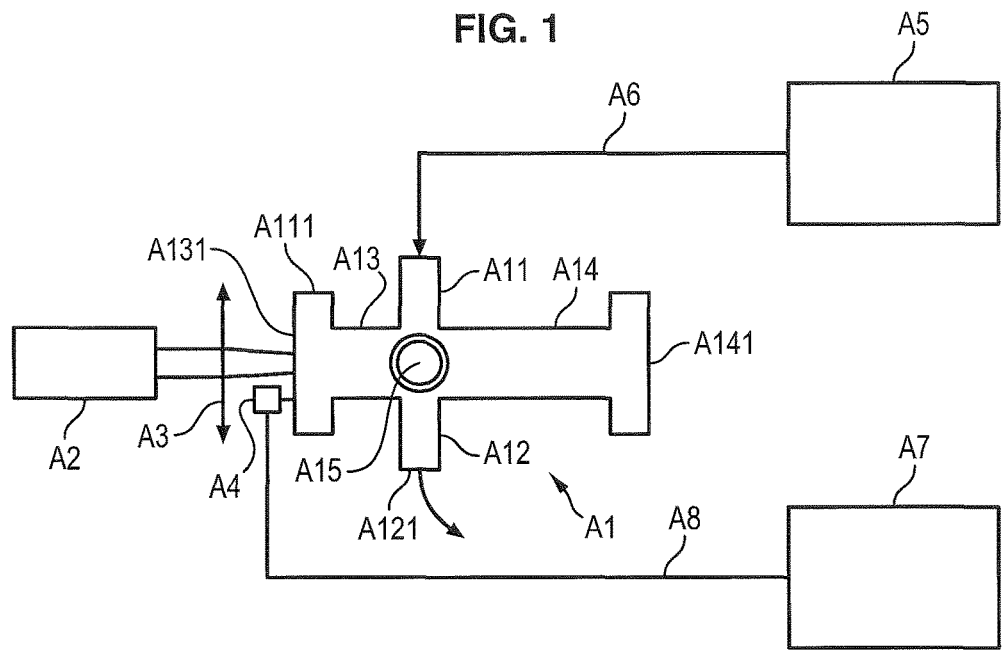

A LIBS system for LIBS analysis is illustrated in FIG. 1 and comprises a nanoparticle synthesis reactor A5, a LIBS cell A1, a laser A2 for emitting a laser beam, a lens A3 for converging the laser beam inside the LIBS cell A1, an optical system A4 for collecting signals coming from the LIBS cell A1, and a spectrometer A7.

Production of nanometric particles within the reactor A5 is based on the interaction of crossed flows between a beam emitted by a laser, for example a carbon dioxide $CO_2$ power laser, and a reactional mixture. The beam excites vibrational states of the molecules (so-called precursors) of the reactional mixture. The energy transmitted from the beam to the molecules is redistributed to the entire reactional mixture by collision. There is then very rapid elevation of the temperature of the reactional mixture which causes thermal decomposition of the molecules, resulting in a so-called "supersaturated" vapour in radicals and in energy. Nanoparticles then form from the radicals by homogeneous germination. The nanoparticles grow by a phenomenon of collision/coalescence growth.

Dissociation and formation of nanoparticles take place in a overlapping volume between the beam and the flow of the reactional mixture observable by way of the production of a flame at this point.

When the nanoparticles exit from this volume, they undergo a quenching effect which stops their growth.

The nanoparticles are then guided to the LIBS cell A1 through an entry conduit A6.

The LIBS cell A1 comprises a reaction chamber and four arms:
- a first arm A11 forming inlet orifice A111 for the smoke;
- a second arm A12 facing the first and forming outlet orifice A121 for evacuating of smoke;
- a third arm A13 closed by a window A131 through which the laser beam intended to form a plasma enters; and
- a fourth arm A14 closed by a cache A141 and facing the third arm A13 is not used.

The LIBS cell A1 also comprises a viewing window A15 for observing the plasma with the naked eye.

In the LIBS cell A1, the nanoparticles behave as a gas and therefore expand inside the reaction chamber and occupy all the space available and form, smoke.

Inside the reaction chamber, the laser beam $F_{laser}$ generated by the laser A2 is focussed by the lens A3. When the laser beam $F_{laser}$ is focussed in the mixture to be analysed there is vaporisation of nanoparticles causing ejection of atoms and forming plasma which expands. During expansion of the plasma, atoms de-energise, causing the emission of light. This light is then received by the optical system A4 which is adapted and placed to the same side as the laser A2. This light is then analysed by the spectrometer A7 connected to the optical system A4 via fibre optics A8 adapted to transport the signal.

On drawback of this LIBS cell results from the fact that the nanoparticles behave as a gas within the reaction chamber. This is why the analysis window A131 of the third arm A13 becomes clogged. The clogged analysis window A131 acts as a filter which blocks part of the laser beam $F_{laser}$. Not all the energy of the laser beam $F_{laser}$ is therefore efficient and only a portion thereof can be used to form the plasma. The formed plasma is therefore less energetic and emits a lower signal. This already weakened signal is further attenuated when it passes back through the analysis window A131 of the third arm towards the optical system A4.

Another drawback, still linked to the gaseous behaviour of the smoke, is the clogging of the viewing window A15 tending to obstruct observation of the plasma with the naked eye.

Figure 2:
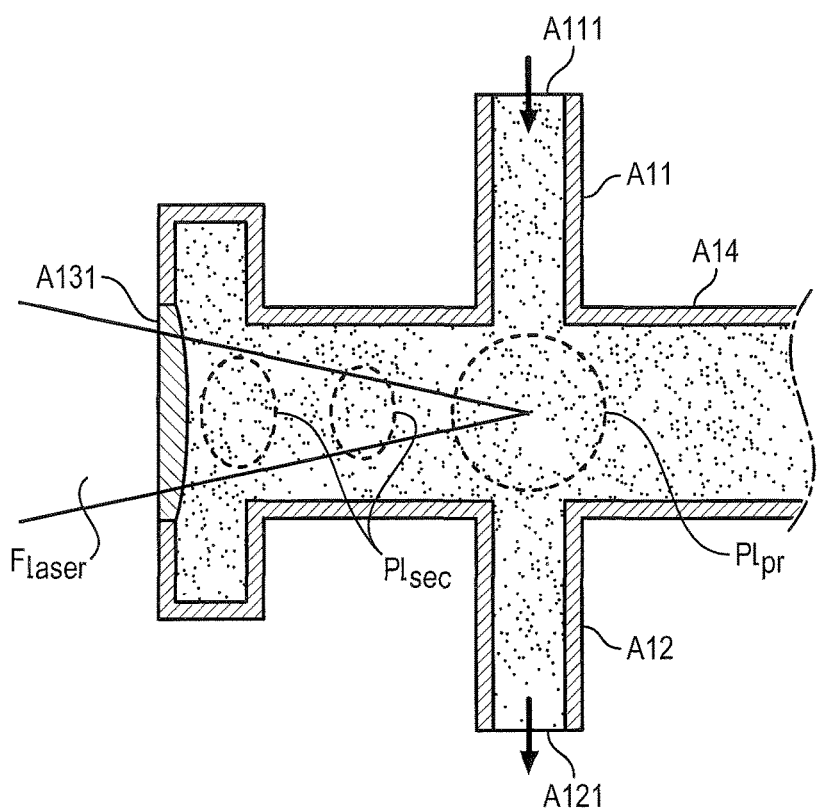

Yet another drawback is that the formed plasma is not limited to the focal point of the laser beam $F_{laser}$, that is to say where the latter is the most highly concentrated. In fact, as particles are present throughout the reaction chamber, secondary plasmas $Pl_{sec}$ can form between the focal point of the laser beam, where the main plasma $Pl_{pr}$ forms, and the analysis window A131 through which the laser beam $F_{laser}$ enters the reaction chamber, as illustrated in FIG. 2. The secondary plasmas $Pl_{sec}$ can be located outside the observation zone by the optical system A4.

Another drawback of the LIBS cell A1 hereinabove is instability of the signals acquired by the optical system A4 and by the spectrometer A7, the origin of which is numerous.

PRESENTATION

The aim of the invention is to overcome at least one of the drawbacks of the prior art presented hereinabove by way of example.

To this aim, the invention provides to a characterisation cell for smoke analysis by optical spectrometry, comprising:
- a reaction chamber;
- an inlet orifice for the inlet of smoke inside the reaction chamber;
- an outlet orifice for the evacuation of smoke from the reaction chamber;

an analysis window for the entry of a laser beam intended to form the plasma inside the reaction chamber;

characterised in that the system also comprises:

a fan for ensuring scanning of inert gas in the vicinity of the analysis window, and a shielding injector for shielded injection of smoke inside the reaction chamber, the shielding being ensured by a jet of inert gas around the smoke.

The advantage is that the signal obtained at output (light emitted by the plasma and passing through the analysis window) is stabilised relative to the prior art.

Other optional and non-limiting features of the cell are:

the cell also comprises an arm extending from the reaction chamber and one free end of which is closed by the analysis window, this arm being formed by two parts of different straight cross-sections, the largest cross-section part being arranged to the side of the analysis window and the smallest cross-section part being arranged to the side of the reaction chamber to form a Venturi and ensure overpressure to the side of the window;

the flow rate of inert gas generated by the fan and optionally the Venturi is adjustable;

the flow rate of inert gas generated by the coaxial shielding injector is adjustable;

the injector is a circular double nozzle having two coaxial orifices, a first having a disc-shaped cross-section for the inlet of smoke and a second having a ring-shaped cross-section which encloses the first for the inlet of inert gas; and a viewing window is provided for observation of the plasma produced inside the reaction chamber during its operation.

The invention also relates to a characterisation system comprising a cell such as that described hereinabove and also a collector downstream of the outlet orifice of the cell recovering the powder after analysis of the latter and a pressure regulator for keeping the pressure constant in the reaction chamber of the cell.

Other optional and non-limiting features of the system are:

the pressure regulator comprises a regulation valve placed downstream of the collector to compensate the loss of charge due to clogging of the filters of the latter;

the regulation valve is connected to a pressure probe placed in the cell for its servo-control; and the fan also ensures scanning of inert gas in the vicinity of the viewing window.

PRESENTATION OF THE DRAWINGS

Figure 3:
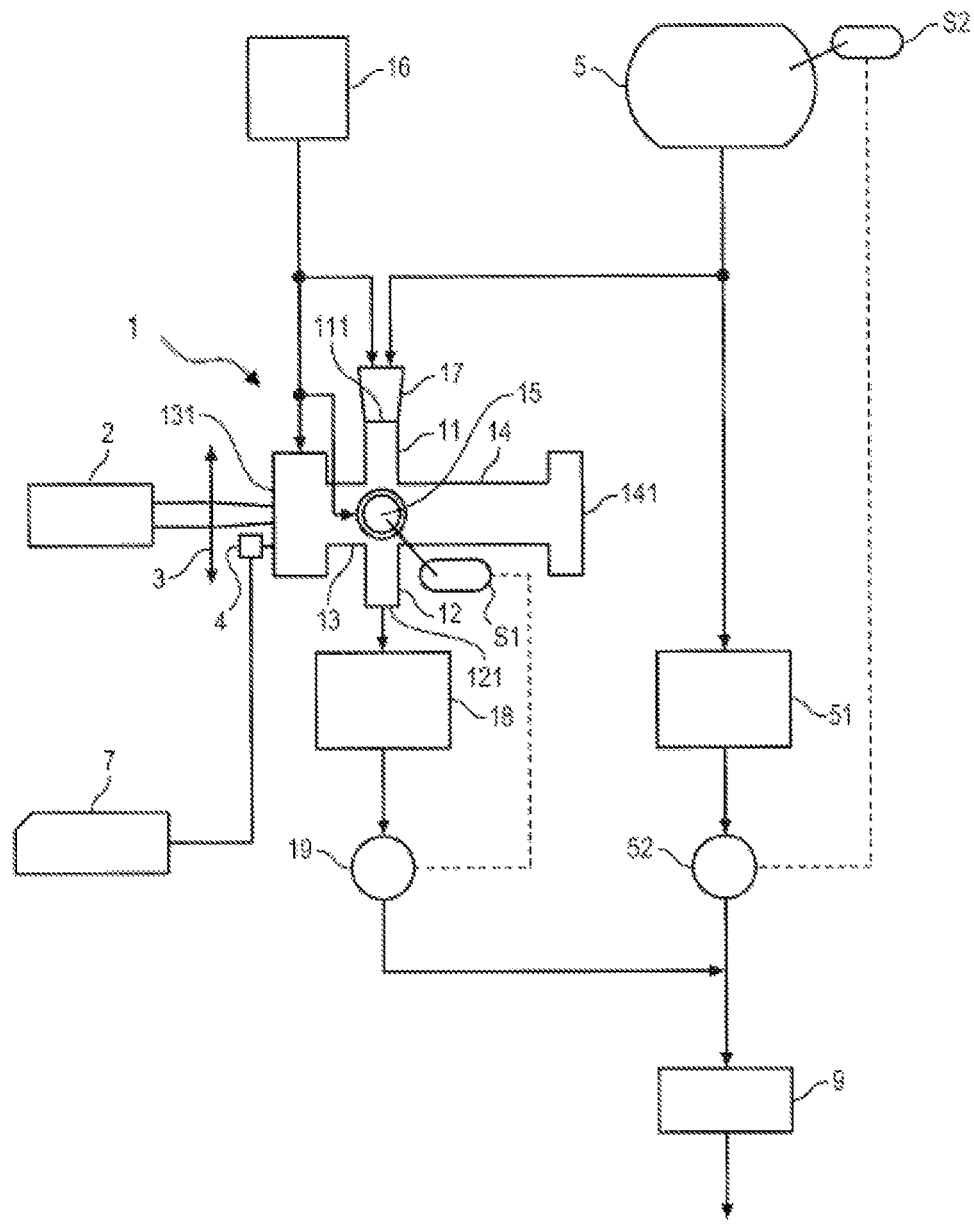
Figure 4:
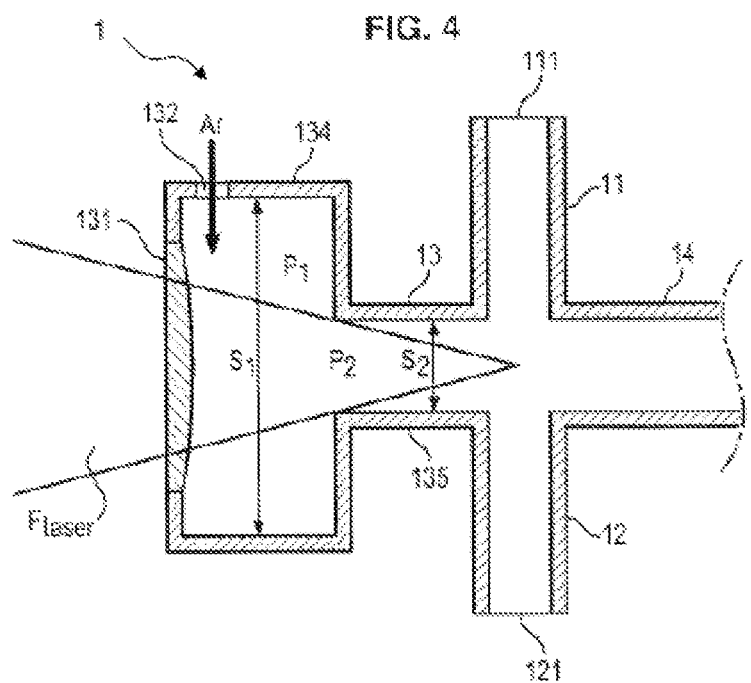
Figure 5:
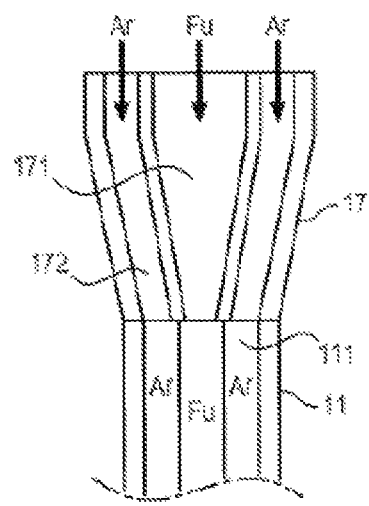

Other aims, features and advantages will emerge from the following detailed description in reference to the drawings given by way of illustration and non-limiting, in which:

FIG. 1 schematically illustrates a conventional LIBS cell;

FIG. 2 schematically illustrates the formation of secondary plasmas in a conventional LIBS cell;

FIG. 3 schematically illustrates an example of a characterisation cell forming the subject matter of the invention and integrated into in a characterisation system;

FIG. 4 schematically illustrates a Venturi such as used in the characterisation cell of FIG. 3;

FIG. 5 schematically illustrates shielding of the smoke such as used in the characterisation cell of FIG. 3;

FIG. 6 is graph illustrating the intensity of the signal measured as a function of a scanning rate inside the characterisation cell of FIG. 3 and a shielding rate of the smoke; and FIG. 7 is a graph illustrating the repeatability of the signal measured as a function of scanning inside the characterisation cell of FIG. 3 and a shielding rate of the smoke.

DETAILED DESCRIPTION

In reference to FIGS. 3 and 4, an example embodiment of a proposed characterisation cell is described hereinbelow. In this example, the characterisation cell is a LIBS system.

The LIBS cell for smoke analysis by plasma created by laser comprises a LIBS cell 1.

The LIBS cell 1 comprises a reaction chamber in which the plasma is formed, a first arm 11 with at its free end an inlet orifice 111 for the inlet of the smoke inside the reaction chamber, a second arm 12 with at its free end an outlet orifice 121 for the evacuation of the smoke from the reaction chamber. The inlet 111 and outlet 121 orifices can be opposite and are arranged advantageously respectively on the upper part and the lower part of the LIBS cell 1.

The LIBS cell 1 further comprises a third arm 13 closed by an analysis window 131 for entry of a laser beam $F_{laser}$ intended to form the plasma inside the reaction chamber.

Facing the third arm 13 a fourth arm 14 closed by a cache 141 can be provided.

The four arms 11, 12, 13 and 14 can be advantageously arranged in to a cross, where the beam entering via the analysis window 131 intersects the smoke entering via the inlet orifice 111 and exiting via the outlet orifice 121 opposite the latter.

The laser beam $F_{laser}$ can ablate the material forming the LIBS cell 1. The fourth arm 14 is therefore selected longer than the third arm 13. Thus chance for the particles which result from ablation by the laser beam $F_{laser}$ of the cache 141 of the fourth arm 14 to pollute the measurements made of the smoke is decreased.

The LIBS cell 1 can also comprise a viewing window 15 to allow an operator to observe the interior of the reaction chamber with the naked eye or by means of a viewing device, for example a video camera connected to a monitor. This viewing window 15 can be arranged on the LIBS cell 1 so that the viewing angle through the viewing window 15 is perpendicular to the incident direction of the laser beam $F_{laser}$ inside the reaction chamber and/or the arrival flow of the smoke via the inlet orifice 111.

The LIBS cell also comprises a fan 16 for ensuring scanning of inert gas near at least the analysis window 131.

This reduces the quantity of smoke in the vicinity of the analysis window 131, therefore decreasing clogging of the analysis window 131.

The fan 16 can be a pump connected by tubes to an inert gas tank, for example argon, on one side, and on the other side to an intake orifice 132 for inert gas located in the third arm 13 in the vicinity of its end closed by the analysis window 131.

To increase the efficiency of the flow of inert gas in the vicinity of the analysis window 131, the third arm 13 can have the form of a Venturi, as illustrated in FIG. 4, i.e. the third arm 13 is divided into two different cross-section parts S1, S2. The first part 134, to the side of its free end, has a cross-section S1 larger than the cross-section S2 of the second part 135 to the side of the reaction chamber. Overpressure ΔP is then generated in the first part 134, further limiting the quantity of smoke in the vicinity of the analysis window 131.

The fan 16 can also be connected to an intake orifice located in the vicinity of the end of the fourth arm 14 which is closed by a cache. This helps balance the flow of argon gas inside the LIBS cell 1.

The fan 16 can also be connected to an intake orifice located in the vicinity of the viewing window 15. This also reduces the clogging of the viewing window 15. In this case, to balance out the flow of inert gas inside the LIBS cell 1, scanning can also be ensured in the same way to the side opposite the viewing window 15.

The flow rate of inert gas of the fan 16 can be adjustable.

The LIBS cell further comprises injector 17 for the coaxial shielded injection of the smoke also the reaction chamber, the shielding being ensured by a jet of inert gas coaxial a the smoke and enclosing the latter.

The shielding of the smoke confines the latter inside the reaction chamber. Therefore, the nanoparticle smoke will not tend to occupy all the space available inside the LIBS cell 1 and especially towards the analysis window 131 and the viewing window 15. This also prevents the formation of secondary plasmas outside the focal point of the laser beam $F_{laser}$.

As illustrated in FIG. 5, the injector 17 can be a double nozzle 17 with truncated cone shape having two coaxial orifices 171 and 172, a first 171 with a disco-shaped cross-section in for the inlet of smoke Fu and a second 172 with a ring-shaped cross-section enclosing the first 171 orifice for the inlet of the inert gas.

In this way the injected inert gas encloses the smoke which is confined inside the cylinder formed by the inert gas. The inert gas is for example argon Ar.

The LIBS cell 1 can form part of a LIBS system also comprising a LIBS collector 18 downstream of the outlet orifice 121 of the LIBS cell 1 and a pressure regulator 19 for keeping the pressure constant in the reaction chamber.

The pressure regulator 19 can be a regulation valve placed downstream of the LIBS collector 18 to compensate the loss of charge due to clogging of the filters of the latter. The regulation valve LIBS 19 is connected to a pressure probe S1 placed inside the LIBS cell 1 for measuring the pressure therein. A servo-control is provided for controlling the regulation valve LIBS 19 as a function of the pressure measured inside the LIBS cell 1. The regulation valve LIBS 19 opens progressively as the LIBS collector 18 is clogged by smoke.

The LIBS system further comprises a reactor 5 for the generation of smoke such as described in the technological background section. The outlet of the reactor 5 is connected to a pump 9 which creates a flow of smoke.

As it leaves the reactor 5, the smoke is led in part to the LIBS cell 1 and in part to a collector 51 of the reactor. Arranged at the outlet of the collector 51 is a regulation valve 52 for regulating the pressure inside the reactor 5 which must be kept constant. The regulation valve 52 is connected to a pressure probe S2 placed inside the reactor 5 for measuring the pressure therein. A servo-control is provided for controlling the regulation valve 52 as a function of the pressure measured inside the reactor 5. The regulation valve 52 opens progressively as the filters of the collector 51 of the reactor 5 become clogged due to nanoparticles.

The collectors 18 and 51 collect nanoparticles of the smoke so that they are not rejected into the atmosphere.

The gas flows leaving the regulation valves 19 and 52 are combined and directed to the pump 9.

The presence of the regulation valve LIBS 19 is needed to conserve a stable observed signal. In fact, in the absence of the regulation valve LIBS 19, the clogging of the collector 51 of the reactor causes opening of the regulation valve 52, which boosts the flow rate in the path outside LIBS cell and decreases the flow rate in the path of the LIBS cell. At the same time, the LIBS collector 18 also clogs up, which varies the pressure in the path of the LIBS cell and therefore inside the LIBS cell 1. The drop in flow rate and the variation in pressure in the path of the LIBS cell make the resulting plasma instable.

Example of Operation

In operation, the pressure inside the reactor 5 is kept below atmospheric pressure to prevent the produced nanoparticles from escaping into the ambient atmosphere, for example, the pressure is servo-controlled at 900 mbar.

The reactor 5 is parameterised to give production of 400 g/h of nanoparticles. The pump 9 sets a rate of 160 m³/h.

A loss of excessive charge between the path outside LIBS and the path of the LIBS cell should be avoided. Indeed, this is harmful for stability of the plasma to be generated.

The pressure inside the LIBS cell 1 can be servo-controlled at 850 mbar. The overall flow rate of inert gas (argon) used for scanning the windows 131 and 15 and shielding the smoke is 30 L/min, distributed as follows: 20 L/min for scanning the windows 131 and 15 and 10 L/min for shielding the smoke.

The laser 2 used is a nanosecond laser of Nd:YAG type. The energy per pulse of the laser 2 is set at 50 mJ. A converging lens 3 is positioned between the laser 2 and the analysis window 131. The laser 2 and the converging lens 3 are positioned so that the focal point of the laser beam $F_{laser}$ emitted by the laser 2 is at the junction of the four arms 11, 12, 13 and 14, or under the inlet flow of the smoke, and opposite the viewing window 15 if the latter is provided on the LIBS cell 2.

The signal emitted by the plasma is collected by the optical system 4 placed at outlet, facing the analysis window 131. The optical system 4 sends the collected signal to a spectrometer 7 which analyses the spectrum of the signal emitted (which is the light of the plasma).

The dimensions of the cell are (from the end of the arms to the centre of the cell, that is, where the plasma is created):
first arm 11: 53 mm
second arm 12: 160 mm
third arm 13: 50 mm
fourth arm 14: 100 mm Comparative Test Comparative tests were conducted on a LIBS cell, the dimensions of which are specified hereinabove for measuring the combined effect of the shielding and of the scanning.

FIG. 6 illustrates a graph illustrating the intensity of the measured signal (in arbitrary unit) as a function of the scanning flow rate used (in L/min) for four different elements: silicon Si, hydrogen H, argon Ar and carbon C.

The intensity of the signal for silicon Si and hydrogen H shows up on the scale of ordinates to the left. The intensity of the signal for argon Ar and carbon C shows up on the scale of ordinates to the right.

The shielding flowrate is selected such that the combined flow rate of the shielding and of the scanning is 30 L/min.

So if the scanning flow rate is 0 L/min, the shielding flow rate is 30 L/min. If the scanning flow rate is 10 L/min, the shielding flow rate is 20 L/min.

FIG. 6 therefore shows that with shielding alone (scanning flow rate is zero), the intensities of the signals for the four elements are much lower than for a shielding flow rate of 10 L/min (or a scanning flow rate of 20 L/min).

This FIG. 6 also shows that with scanning alone (shielding flow rate is zero), the intensities of the signals for the four elements are lower than for a shielding flow rate of 10 L/min (or a scanning flow rate of 20 L/min).

The conditions of shielding flow rate at 10 L/min and scanning flow rate at 20 L/min are close to the optimum and produce signal intensities close to the maximum.

FIG. 7 shows the combined effect of shielding and scanning on the repeatability of the signal. The repeatability is given in ordinates for four elements (same as for FIG. 6) and is expressed in relative standard deviation of the intensity of lines and calculated over fifty spectra, one spectrum resulting from integration of the signal over thirty shots by a laser. The lower the standard deviation the better the repeatability.

The shielding flow rate is selected such that the combined flow rate of shielding and scanning is 30 L/min.

It is noticed that the repeatability of the measured signals is better when the shielding and the scanning are combined relative to the use of the shielding alone or the scanning alone with a low value translating considerable repeatability. When the scanning flow rate is 20 L/min and that of shielding is 10 L/min the repeatability is close to the minimum.

Both FIGS. 6 and 7 therefore show that the effect of shielding alone and of scanning alone are not added together, but much more, signal quality is unexpectedly improved.

Even though the description has been given in reference to a LIBS cell, the invention is not limited to the latter and also relates to other cells and especially those adapted for the following spectrometries:
 laser-induced fluorescence;
 fluorescence spectrometry;
 absorption spectrometry;
 Raman spectrometry; and
 infrared spectrometry.

The invention claimed is:
1. A characterisation system comprising:
 a characterisation cell for smoke analysis by optical spectrometry, comprising:
  a reaction chamber;
  an inlet orifice for the inlet of smoke into the reaction chamber;
  an outlet orifice for the evacuation of smoke from the reaction chamber;
  an analysis window for entry of a laser beam intended to form the plasma inside the reaction chamber;
  a fan for ensuring scanning of inert gas in the vicinity of the analysis window; and
  a shielding injector coaxially aligned with the inlet orifice configured to coaxially inject smoke shielded by a jet of inert gas around the smoke into the reaction chamber;
 a collector downstream of the outlet orifice of the cell configured to recover the smoke after its analysis;
 a pressure regulator for keeping the pressure constant in the reaction chamber of the cell,
 wherein the pressure regulator comprises a regulation valve placed downstream of the collector to compensate for a loss of charge due to clogging of filters of the collector,
 wherein the regulation valve is connected to a pressure probe placed in the cell for measuring the pressure therein for its servo-control, and
 wherein the regulation valve is servo-controlled as a function of the pressure measured inside the cell and which is adapted to open progressively as the collector gets clogged;
 a reactor for the generation of smoke;
 a second collector positioned downstream of the reactor;
 a second regulation valve for regulating the pressure inside the reactor;
 wherein the second regulation valve is placed downstream of the second collector,
 wherein the second regulation valve is connected to a second pressure probe placed in the reactor for measuring the pressure therein for its servo-control, and
 wherein the second regulation valve is servo-controlled as a function of the pressure measured inside the reactor and which is adapted to open progressively as the second collector gets clogged.

2. The system of claim 1, wherein the cell further comprises an arm extending between the reaction chamber and the analysis window, the arm being formed in two parts of different cross-sections, the larger cross-section part being arranged nearer the analysis window and the smaller cross-section part being arranged nearer the reaction chamber to form a Venturi and to ensure overpressure nearer the window.

3. The system of claim 1, wherein the flow rate of inert gas generated by the fan is adjustable.

4. The system of claim 1, wherein the flow rate of inert gas generated by the coaxial shielding injector is adjustable.

5. The system of claim 1, wherein the injector is a circular double nozzle having first and second coaxial orifices, the first orifice having a disc-shaped cross-section for the inlet of smoke, and the second orifice having a ring-shaped cross-section which encloses the first orifice for the inlet of inert gas.

6. The system of claim 1, wherein the cell further comprises a viewing window for observation of the plasma produced inside the reaction chamber during its operation.

7. The system of claim 1, wherein the fan also ensures scanning of inert gas in the vicinity of the viewing window.

8. The system of claim 1, wherein the flow rate of inert gas generated by the Venturi is adjustable.

9. The system of claim 1, wherein the cell further comprises an arm extending between the reaction chamber and the inlet orifice.

10. The system of claim 1, wherein the cell further comprises an arm extending between the reaction chamber and the outlet orifice.

11. The system of claim 1, wherein the cell further comprises a first arm extending between the reaction chamber and the inlet orifice, a second arm extending between the reaction chamber and the outlet orifice, and a third arm extending between the reaction chamber and the analysis window.

12. The system of claim 11, wherein the first and second arms extend along a first axis, and the third arm extends along a second axis that is perpendicular to the first axis.

13. The system of claim 11, wherein the third arm is formed in two parts of different cross-sections, the larger cross-section part being arranged nearer the analysis window and the smaller cross-section part being arranged nearer the reaction chamber to form a Venturi and to ensure overpressure nearer the window.

14. The system of claim 1, wherein the smoke is a smoke of nanoparticles.

15. The system of claim 1, wherein the second regulation valve regulates the pressure inside the reactor so as to keep said pressure constant.

16. The system of claim 1, wherein the second regulation valve is placed at the outlet of the second collector.

17. The system of claim 1, wherein the second regulation valve is adapted to open progressively as filters of the second collector gets clogged due to nanoparticles.

18. The system of claim 1, wherein an outlet of the reactor is connected to a pump which creates a flow of smoke.

* * * * *